US008779003B2

(12) United States Patent
Hung

(10) Patent No.: US 8,779,003 B2
(45) Date of Patent: Jul. 15, 2014

(54) METHOD AND COMPOSITION FOR PROLONGING ANALGESIC EFFECT OF LOCAL ANESTHETIC

(75) Inventor: Yu-Chun Hung, New Taipei (TW)

(73) Assignee: Mackay Memorial Hospital, Taipei (TW)

( * ) Notice: Subject to any disclaimer, the term of this patent is extended or adjusted under 35 U.S.C. 154(b) by 84 days.

(21) Appl. No.: 13/340,330

(22) Filed: Dec. 29, 2011

(65) Prior Publication Data

US 2013/0172387 A1 Jul. 4, 2013

(51) Int. Cl.
| | | |
|---|---|---|
| *A01N 37/18* | (2006.01) | |
| *A61K 31/165* | (2006.01) | |
| *A61K 31/16* | (2006.01) | |
| *A01N 35/00* | (2006.01) | |
| *A61K 31/11* | (2006.01) | |
| *C07C 233/00* | (2006.01) | |
| *C07C 235/00* | (2006.01) | |
| *C07C 237/00* | (2006.01) | |
| *C07C 239/00* | (2006.01) | |
| *C07C 321/00* | (2006.01) | |
| *C07C 323/00* | (2006.01) | |
| *C07C 381/00* | (2006.01) | |
| *C07C 47/00* | (2006.01) | |

(52) U.S. Cl.
USPC ........... 514/617; 514/623; 514/625; 514/701; 564/161; 564/188; 564/189; 564/190; 564/192; 568/425

(58) Field of Classification Search
CPC .... A61K 31/167; A61K 31/11; C07C 47/232; C07C 233/01; C07C 233/57; C07C 233/64; C07C 237/06
USPC .......... 514/617, 623, 625, 701; 564/161, 188, 564/189, 190, 191, 192; 568/425
See application file for complete search history.

(56) References Cited

U.S. PATENT DOCUMENTS 4,997,853 A * 3/1991 Bernstein ...................... 514/626
2011/0086818 A1 4/2011 Bean

FOREIGN PATENT DOCUMENTS

WO   WO 2011057387 A1 * 5/2011

* cited by examiner

*Primary Examiner* — Sarah Pihonak
(74) *Attorney, Agent, or Firm* — Muncy, Geissler, Olds & Lowe, P.C.

(57) ABSTRACT

Disclosed herein is a method for prolonging analgesic effect of a membrane permeable local anesthetic in a subject in need thereof. The method uses cinnamaldehyde as an adjuvant which, when administered prior to or simultaneously with the administration of a local anesthetic, prolongs the analgesic effect of the local anesthetic. Also disclosed herein is a method for providing analgesic effect in a subject in need thereof. The method uses cinnamaldehyde as an analgesic compound which, when administered alone to the subject in an analgesically effective amount, provides the analgesic effect.

7 Claims, 3 Drawing Sheets
(1 of 3 Drawing Sheet(s) Filed in Color)

METHOD AND COMPOSITION FOR PROLONGING ANALGESIC EFFECT OF LOCAL ANESTHETIC

BACKGROUND OF THE INVENTION

1. Field of the Invention

The present disclosure features methods and compositions related to prolonging analgesic effect of local anesthetics and/or providing analgesic effect. More particularly, the disclosure invention relates to the use of cinnamaldehyde as an adjuvant to prolong analgesic effect of a local anesthetic and as an analgesic drug.

2. Description of Related Art

A local anesthetic may reversibly prevent the generation and/or the conduction of the nerve impulse in the region to which it is applied, without affecting consciousness of the subject. The prevention of the generation and/or conduction of the nerve impulse may result in the regional loss of bodily sensations, including pain, temperature, touch, and proprioception. The degree of anesthesia (including analgesia) depends on the choice and concentration of the local anesthetics and integrity of the application site. Therefore, it has long been desired to provide a more effective local anesthetic composition in terms of the duration and/or the extent of analgesia.

Transient receptor potential vanilloid (TRPV) is a family of TRP ion channels. The first member of this family being identified is TRPV1, which may be activated by a wide variety of stimuli, such as heat, acidic conditions, and endocannabinoid anandamide. Capsaicin is a TRPV1 agonist and previous studies have demonstrated a nociceptive-selective, long-lasting nerve blockade by first injecting the nearly membrane-impermeable local anesthetic QX-314, then followed by capsaicin. However, one concern is that capsaicin causes burning sensation upon injection, thereby limiting its use in clinical medicine.

In view of the foregoing, there exists in the art a need for a novel method and composition that prolongs the analgesic effect of local anesthetics.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on, at least in part, the discovery that cinnamaldehyde, when administered preceding or simultaneously with the administration of a local anesthetic, prolongs the duration of analgesia and enhances the degree of analgesia, as compared with that produced by the local anesthetic alone.

In view of the foregoing, one aspect of the invention pertains to a method for prolonging analgesic effect of a membrane permeable local anesthetic in a subject in need thereof. According to one embodiment of the present disclosure, the method comprises administering to the subject an anesthetically effective amount of the membrane permeable local anesthetic and an effective amount of cinnamaldehyde for prolonging the analgesic effect of the membrane permeable local anesthetic in the subject, in the absence of a membrane impermeable compound that inhibits one or more voltage-gated ion channels when applied to the internal face of said channels but does not substantially inhibit said channels when applied to the external face of said channels.

According to one embodiment of the present disclosure, the cinnamaldehyde is administered prior to the administration of the membrane permeable local anesthetic. In an alternative embodiment, the membrane permeable local anesthetic and the cinnamaldehyde are administered simultaneously.

According to various embodiment of the present disclosure, the membrane permeable local anesthetic is an amide local anesthetic. Examples of amide local anesthetic include but are not limited to, lidocaine, mepivacaine, prilocaine, bupivacaine, levobupivacaine, ropivacaine, dibucaine, and articaine.

According to embodiments of the present disclosure, the membrane permeable local anesthetic and the cinnamaldehyde are administered subcutaneously, neuraxially, orally, topically, transdermally, or nasally.

Another aspect of the invention pertains to a composition for prolonging analgesic effect of a membrane permeable local anesthetic in a subject in need thereof.

According to one embodiment of the present disclosure, the composition comprises an anesthetically effective amount of a membrane permeable local anesthetic, and an effective amount of cinnamaldehyde for prolonging the analgesic effect of the membrane permeable local anesthetic in the subject, wherein the composition is characterized in not having a membrane impermeable compound that inhibits one or more voltage-gated ion channels when applied to the internal face of said channels but does not substantially inhibit said channels when applied to the external face of said channels.

According to various embodiment of the present disclosure, the membrane permeable local anesthetic is an amide local anesthetic. Examples of amide local anesthetic include but are not limited to, lidocaine, mepivacaine, prilocaine, bupivacaine, levobupivacaine, ropivacaine, dibucaine, and articaine.

According to embodiments of the present disclosure, the composition is suitable for use in subcutaneous, neuraxial, oral, topical, transdermal, or nasal administration.

The present invention is also directed to a method for prolonging analgesic effect of a membrane permeable local anesthetic in a subject in need thereof. According to one embodiment of the present disclosure, the method comprises administering to the subject an effective amount of the composition according to the above aspect/embodiments of the present disclosure to prolong analgesic effect of the membrane permeable local anesthetic in the subject. According to optional embodiments of the present disclosure, the membrane permeable local anesthetic is lidocaine or bupivacaine.

The present invention is also directed to a method for providing analgesic effect in a subject in need thereof. According to one embodiment of the present disclosure, the method comprises administering to the subject an analgesically effective amount of cinnamaldehyde to provide the analgesic effect in the subject.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE PREFERRED EMBODIMENTS

Figure 1:
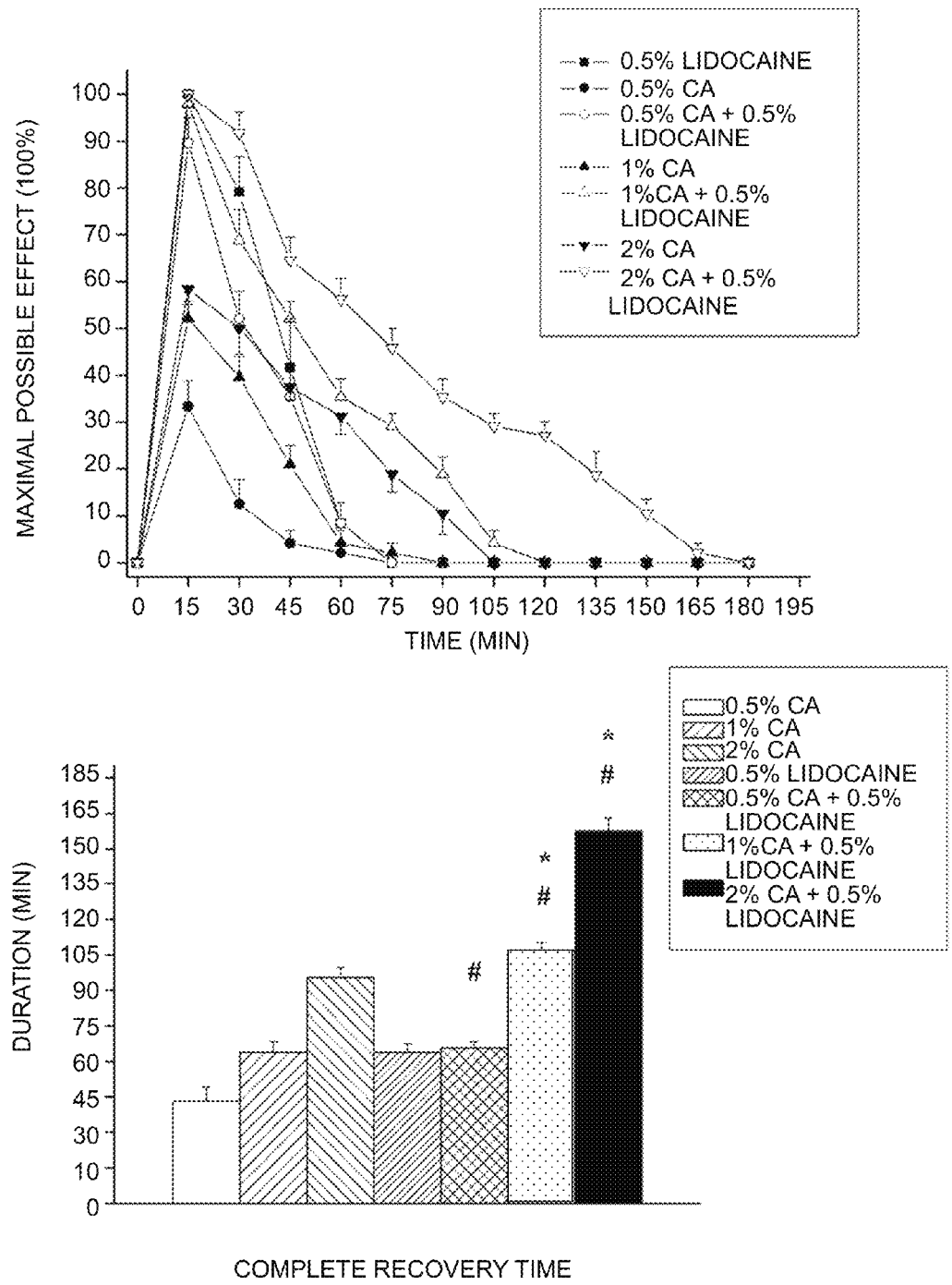
FIG. 1 depicts the analgesia effect produced by various treatment in accordance with one example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "local anesthesia" refers to anesthesia characterized by the loss of sensation only in the area of the body where an anesthetic agent or a combination of anesthetic agents is administered. As used herein, the term "anesthetically effective amount" refers to an amount of an anesthetic agent or a combination of anesthetic agents that produces an anesthetic effect, e.g., a partial or total loss of sensation, inhibition of sensory perception, or inhibition of motor function. Preferably, the anesthetically effective amount produces minimal toxic side-effects. The term "local anesthetic" refers to an anesthetic agent that induces local anesthesia by reversibly inhibiting peripheral nerve excitation and/or transmission. The term "membrane permeable local anesthetic" refers to a local anesthetic that is capable of penetrating a cell membrane by crossing the lipid bilayers or passing through the voltage-gated ion channels by activating the channels. The term "membrane impermeable compound" as used herein to indicate that the compound, when present outside the cell membrane, neither crosses the lipid bilayers of an intact cell nor activates the voltage-gated ion channels on the cell membrane to a significant or detectable degree. However, the membrane impermeable compound may pass through the voltage-gated ion channels once these channels are activated. In particular, the "membrane impermeable compound" is used herein in reference to the compound that inhibits one or more voltage-gated ion channels when applied to the internal face of said channels but does not substantially inhibit said channels when applied to the external face of said channels.

The terms "analgesia" or "analgesic effect" is used herein to describe states of reduced pain perception, including absence from pain sensations as well as states of reduced or absent sensitivity to noxious stimuli. The term analgesia encompasses the term "antinociception", which is used in the art as a quantitative measure of analgesia or reduced pain sensitivity in animal models. In the context of the present disclosure, such states of reduced or absent pain perception are induced by the administration of a local anesthesia. The term "prolonging the analgesic effect", as used herein means that the analgesic effect occurs or is observed over a comparatively or relatively longer time interval than a suitable control. The term "promoting the analgesic effect", as used herein means that the duration and extent of the analgesic effect are improved over a suitable control.

The term "administered", "administering" or "administration" are used interchangeably herein to refer means either directly administering a compound or a composition of the present disclosure, or administering a prodrug, derivative or analog which will form an equivalent amount of the active compound within the body.

The term "subject" refers to an animal including the human species that is treatable with the compositions and/or methods of the present disclosure. The term "subject" is intended to refer to both the male and female gender unless one gender is specifically indicated.

Transient receptor potential ankyrin subfamily member 1 (TRPA1) is one of the transient receptor potential channel family. This receptor is a non-selective calcium channel activated by noxious cold temperature, mechanical stimuli, and inflammation. Cinnamaldehyde is an organic compound extracted from cinnamon bark that gives cinnamon its flavor and odor. It serves as an agonist of TRPA1 and enhances inhibitory as well as excitatory synaptic transmissions in the nervous system. However, the role of cinnamaldehyde on cutaneous analgesia remains unclear.

The present disclosure is the first to demonstrate that cinnamaldehyde, when administered together with at least one membrane permeable local anesthetic, promotes the analgesic effect of the local anesthetic, as compared with that produced by the local anesthetic alone. In view of this discovery, the present disclosure proposes methods and compositions for prolonging the analgesic effect of the local anesthetic.

According to one embodiment of the present disclosure, the method comprises administering to the subject an anesthetically effective amount of the membrane permeable local anesthetic and cinnamaldehyde in an amount effective for prolonging the analgesic effect of the membrane permeable local anesthetic in the subject. It should be noted that according to principles and spirits of the present invention, the membrane permeable local anesthetic and cinnamaldehyde are administered in the absence of a membrane impermeable compound that inhibits one or more voltage-gated ion channels when applied to the internal face of said channels but does not substantially inhibit said channels when applied to the external face of said channels.

According to one embodiment of the present disclosure, the cinnamaldehyde is administered prior to (e.g., at least 1, 2, 3, 4, 5, 6, 7, 8, 9, 10, 15, 20, 25, or 30 minutes) the administration of the membrane permeable local anesthetic. For example, the cinnamaldehyde is administered about 10 minutes before the administration of the membrane permeable local anesthetic according to the working examples hereinbelow. Alternatively, the membrane permeable local anesthetic and the cinnamaldehyde are administered substantially simultaneously.

According to various embodiment of the present disclosure, the membrane permeable local anesthetic is an amide local anesthetic. Examples of amide local anesthetic include but are not limited to, lidocaine (2-(diethylamino)-N-(2,6-dimethylphenyl)acetamide), mepivacaine (N-(2,6-dimethylphenyl)-1-methylpiperidine-2-carboxamide), prilocaine (N-(2-methylphenyl)-2-(propylamino)propanamide), bupivacaine (1-butyl-N-(2,6-dimethylphenyl)piperidine-2-carboxamide), levobupivacaine ((2S)-1-butyl-N-(2,6-dimethylphenyl)piperidine-2-carboxamide), ropivacaine ((2S)—N-(2,6-dimethylphenyl)-1-propylpiperidine-2-carboxamide), dibucaine (2-butoxy-N-[2-(diethylamino)ethyl]quinoline-4-carboxamide), and articaine ((RS)-methyl 4-methyl-3-(2-propylaminopropanoylamino)thiophene-2-carboxylate).

The exact amount of the cinnamaldehyde required for effectively prolonging the analgesic effect of the local anesthetic will vary depending on the choice local anesthetic. According to various embodiments of the present disclosure, the lidocaine and the cinnamaldehyde are administered at a molar ratio of about 1:2 to 1:10; equivalent to a weight ratio of about 1:1 to 1:4. Preferably, the molar ratio is about 1:4 to 1:10. Specifically, the molar ratio of lidocaine to cinnamaldehyde is about 1:2, 1:3, 1:4, 1:5, 1:6, 1:7, 1:8, 1:9, or 1:10. According to other embodiments of the present disclosure, the bupivacaine and the cinnamaldehyde are administered at a molar ratio of about 1:20 to 1:85; equivalent to a weight ratio of about 1:8 to 1:32. Preferably, the molar ratio is about 1:40 to 1:85. Specifically, the molar ratio of bupivacaine to cinnamaldehyde is about 1:20, 1:25, 1:30, 1:35, 1:40, 1:45, 1:50, 1:55, 1:60, 1:65, 1:70, 1:75, 1:80, or 1:85.

The concentration of cinnamaldehyde used can vary according to the type and dosage of the membrane permeable local anesthetic to be co-administered. In general, a higher concentration of cinnamaldehyde can be used when co-administered with a short-onset local anesthetic. The concentration of cinnamaldehyde can range between 0.05% to about 5% by weight. In some cases, cinnamaldehyde is used at a concentration between about 0.5% to about 2% by weight; and preferably, about 1% to about 2% by weight. Specifically, the concentration of cinnamaldehyde used in the working examples provided hereinbelow is about 0.5%, 1%, and 2% by weight.

Any suitable mode of administration may be used to accomplish the present method. For example, the administration of the membrane permeable local anesthetic and cinnamaldehyde may be subcutaneous, neuraxial, oral, topical, transdermal (including transmucosal), or nasal.

As described herein, the cinnamaldehyde is administered to a subject at an amount sufficient to achieve the desired effect (e.g., prolonged analgesia). In general, the effective amount may be determined by either in vitro or in vivo methods. According to embodiments of the present disclosure, the subject is a human. The interrelationship of dosages for animals and humans is calculated in accordance with the well-known Meeh-Rubner equation. Dosage values may vary according to factors such as the disease state, age, sex, and weight of the individual.

For a human subject, the effective amount of cinnamaldehyde is about 2-10 mg/kg; preferably, about 4-10 mg/kg. According to embodiments of the present disclosure, the effective amount of the cinnamaldehyde may be about 2, 2.5, 3, 3.5, 4, 4.5, 5, 5.5, 6, 6.5, 7, 7.5, 8, 8.5, 9, 9.5, or 10 mg/kg.

According to embodiments of the present disclosure, the composition for prolonging analgesic effect of a membrane permeable local anesthetic in a subject in need thereof comprises an anesthetically effective amount of a membrane permeable local anesthetic or a pharmaceutically acceptable salt thereof, and an effective amount of cinnamaldehyde or a pharmaceutically acceptable salt thereof for prolonging the analgesic effect of the membrane permeable local anesthetic in the subject; and without the presence of any membrane impermeable compound that inhibits one or more voltage-gated ion channels when applied to the internal face of said channels but does not substantially inhibit said channels when applied to the external face of said channels.

Examples of membrane permeable local anesthetics suitable for use herein, the effective amount and concentration of cinnamaldehyde, and the molar ratio between the local anesthetic and cinnamaldehyde are described hereinabove, and thus are omitted herein for the sake of brevity.

The composition may be formulated in various dosage forms for subcutaneous, neuraxial, oral, topical, transdermal (including transmucosal), or nasal administration.

For subcutaneous administration, the membrane permeable local anesthetic and cinnamaldehyde may be combined respectively or collectively with a pharmaceutically acceptable carrier such as a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. Other pharmaceutically acceptable carriers, adjuvants, and vehicles that may be used in the compositions described herein can include, without limitation, ion exchangers, alumina, aluminum stearate, lecithin, serum proteins (e.g., human serum albumin), buffer substances (e.g., phosphates, citrate, glycine, sorbic acid, potassium sorbate, and the like), partial glyceride mixtures of saturated vegetable fatty acids, water, salts, or electrolytes (e.g., protamine sulfate, disodium hydrogen phosphate, potassium hydrogen phosphate, sodium chloride, zinc salts, and the like), colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat. Formulations may be present in unit or multi-dose containers such as pre-filled syringes, sealed ampoules, or vials.

For topical administration to the epidermis, the membrane permeable local anesthetic and the cinnamaldehyde may be formulated respectively or collectively as creams, gels, ointments, or lotions or as transdermal patches. Such compositions can, for example, be formulated with an aqueous or oily base with the addition of suitable thickening, gelling, emulsifying, stabilizing, dispersing, suspending, and/or coloring agents. For transdermal administration, the membrane permeable local anesthetic and the cinnamaldehyde may be combined respectively or collectively with skin penetration enhancers such as propylene glycol, polyethylene glycol, isopropanol, ethanol, oleic acid, N-methylpyrrolidone, which increase the permeability of the skin to the compounds, and permit the active compounds to penetrate through the skin.

For administration via the oral or nasal inhalation routes, typically the active compounds will be in a suitable pharmaceutical formulation and may be delivered using a mechanical form including, but not restricted to an inhaler, nebulizer device or a nasal spray. Further, where the oral or nasal inhalation route is used, administration by a SPAG (small particulate aerosol generator) may be used.

The present invention is also directed to a method for prolonging analgesic effect of a membrane permeable local anesthetic in a subject in need thereof. According to one embodiment of the present disclosure, the method comprises administering to the subject an effective amount of the composition according to the above aspect/embodiments of the present disclosure to prolong analgesic effect of the membrane permeable local anesthetic in the subject. According to optional embodiments of the present disclosure, the membrane permeable local anesthetic is lidocaine or bupivacaine.

The present disclosure is also the first to demonstrate that cinnamaldehyde, when administered alone to a subject, provides analgesic effect in the subject. In view of this discovery, the present disclosure proposes methods and compositions for providing the analgesic effect in a subject in need thereof.

According to one embodiment of the present disclosure, the method comprises administering to the subject an analgestically effective amount of the cinnamaldehyde so as to provide the analgesic effect in the subject.

Any suitable mode of administration, such as those described hereinabove, may be used to accomplish the present method. Therefore, it is feasible to formulate cinnamaldehyde into any formulation appropriate for desired route of administration; for example, cinnamaldehyde could be formulated into the formulations exemplified hereinabove.

For a human subject, the analgestically effective amount of cinnamaldehyde is about 2-10 mg/kg; preferably, about 4-10 mg/kg. According to embodiments of the present disclosure, the effective amount of the cinnamaldehyde may be about 2, 2.5, 3, 3.5, 4, 4.5, 5, 5.5, 6, 6.5, 7, 7.5, 8, 8.5, 9, 9.5, or 10 mg/kg.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Materials

Cinnamaldehyde was purchased from Sigma-Aldrich (St Louis, Mo.); lidocaine and bupivacaine hydrochloride were purchased from AstraZeneca USA (Westborough, Mass.). Dimethyl sulfoxide (DMSO, Merck, Darmstadt, Germany) was diluted with 5% dextrose solution as the vehicle of cinnamaldehyde (pH ranged from 4.8-5.0). The final concentrations of DMSO and dextrose solution were 40% and 3% respectively. Bupivacaine and lidocaine hydrochloride were dissolved in normal saline (pH ranged from 5.8-6.5). Upon local injection, the relatively low pH of these solutions is likely to be buffered quickly by the tissue fluid, which has a pH of 7.4. All drug solutions were freshly prepared before each injection.

Subcutaneous Injection

The animal experimental protocol was approved by the Animal Committee of Mackay Memorial Hospital in Taipei, Taiwan. Male Sprague-Dawley rats were purchased from BioLasco (Taipei, Taiwan) and kept in an air-conditioned animal shelter at room temperature of 22° C. to 24° C. with controlled level of humidity (40% to 50%) in a 12-hour light-dark cycle. At the time of injection, each rat weighed between 250 g to 300 g and showed no sign of neurobehavioral impairment. The rats were randomly assigned to treatments with a size of 8 rats per group. All rats were briefly anesthetized by inhalation of 2% isoflurane (Abbott Laboratories, North Chicago, Ill.). The back of each rat was carefully shaved with a razor and was left with no injuries. After the induction of inhalation anesthesia, the drugs were injected subcutaneously in the thoracolumbar region. The injections caused a circular elevation of the skin, creating a wheal of approximately 2 cm in diameter. This wheal was marked within a minute after the injection. Using a very fine needle (30-gauge), 0.6 ml of cinnamaldehyde solution (0.5%, 39.7 mM; 1%, 79.4 mM; or 2%, 158.9 mM), lidocaine (0.5%, 18.5 mM) and bupivacaine (0.0625%, 1.9 mM) were respectively injected subcutaneously in rats' shaved dorsal skin (n=8 per group). In combination treatments, 0.6 ml of lidocaine (0.5%) and bupivacaine (0.0625%) were each given 10 minutes after the injection of 0.6 ml of cinnamaldehyde (0.5%, 1%, or 2%).

Neurobehavioral Examination

Before the experiments were conducted, the animals were handled daily for up to 14 days to familiarize them with the behavioral investigator, the experimental environment, and the specific experimental protocols. A noxious pinprick test was used to measure the analgesic effect of the cutaneous trunci muscle reflex (CTMR), which is characterized by reflex movements of the skin over the back produced by twitches of the lateral thoracispinal muscles in response to local dorsal cutaneous stimulations. The von Frey filament (26.0 g) was affixed to an 18-gauge needle to standardize the stimulus intensity and to test the neurobehavioral examination. Six pinpricks were applied in the marked areas every 15 minutes after each drug administration until the rats were fully recovered from the block. Six pinpricks per test were sufficient enough to obtain reproducible results in rats among different study groups, while avoiding injury of the skin during repeated testing. The efficacy of the drugs was quantitatively evaluated an expressed by the number of times the pinprick failed to elicit a response. The total absence of CTMR response was defined as a complete blockade with 100% of maximum possible effect (MPE). Three CTMR pinprick responses indicated a 50% of MPE, while 0% of observed MPE would show the presence of all six CTMR pinprick responses. The complete recovery time (CRT) is defined as the time period when the presence of all six pinprick responses returned with 0% of MPE. All CTMR responses observed in rats were under stable vital signs. To determine skin irritation (such as necrosis, swelling and inflammation), assessment in any macroscopic changes of the skin color and texture was further studied. Systemic side effects such as sedation, agitation, and respiratory distress were also evaluated. The observer was not informed about the drugs used.

Histology

To determine the toxicity of the present composition to the subcutaneous tissue, skin was excised from the injected area of anesthetized rats two days later. The skin cross-section samples were fixed in 4% paraformaldehyde overnight and stained with hematoxylin and eosin.

Statistical Analysis

The statistical difference between the treatment groups was tested by using Mann-Whitney Rank Sum Test to evaluate the analgesic degree of MPE. Microcal Origin version 7 (Microcal Software, Northampton, Mass.) and SigmaStat (Systat Software, Inc., Chicago, Ill.) were used to calculate the values of MPE, creating figures and analyzing statistics. A p value of less than 0.05 was defined significant. All data are presented as mean±SE.

Example I

Dose-Response Analysis of Single Injection of Cinnamaldehyde

Figure 2:
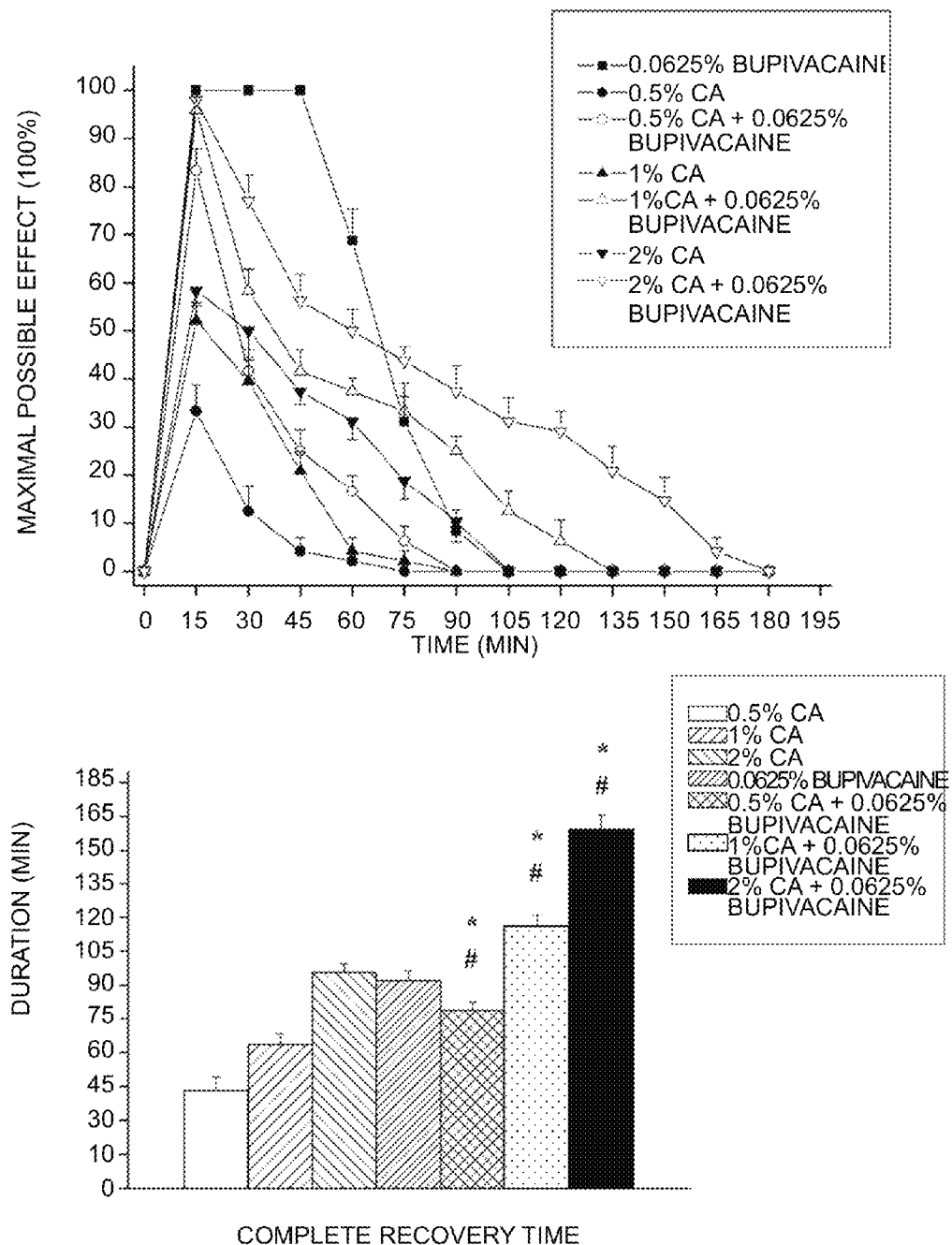
FIG. 2 depicts the analgesia effect produced by various treatment in accordance with another example of the present disclosure.

Cinnamaldehyde (CA) alone at concentrations of 0.5%, 1%, and 2%, respectively produced dose-dependent analgesic effect (FIG. 1 and FIG. 2; Table 1) in rats. In particular, the respective time of complete recovery after single injections of 0.5%, 1%, and 2% cinnamaldehyde was 43.13±5.97, 63.75±4.70, and 95.63±3.95 minutes.

In terms of skin irritation, neither obvious change of skin color nor injury was observed. DMSO, the vehicle of cinnamaldehyde, exhibited no analgesic effect.

Intragroup comparison demonstrated significant differences among the different dosing groups. In particular, the time of complete recovery of rats treated with 1% or 2% cinnamaldehyde plus 0.5% lidocaine was significantly prolonged over cinnamaldehyde or lidocaine alone. However, while rats treated with 0.5% cinnamaldehyde plus 0.5% lidocaine also exhibited significantly prolonged time of complete recovery as compared to 0.5% cinnamaldehyde alone, yet it was not the case when compared to 0.5% lidocaine (FIG. 1; Table 1). There was no obvious injury at the injected area after co-administrations of cinnamaldehyde and lidocaine.

Example III

Co-Administration of Cinnamaldehyde and Bupivacaine

The injection of bupivacaine (0.0625%) alone elicited complete nociceptive block that lasted for approximately 45 minutes and the time of complete recovery was 91.88±4.43 minutes. To investigate the prolonged analgesic effects induced by the co-administration of cinnamaldehyde and bupivacaine, bupivacaine (0.0625%) was given 10 minutes after the application of cinnamaldehyde at concentrations of 0.5%, 1%, and 2%, respectively. Complete nociceptive block to pinpricks was increased after co-administrations of all selected concentrations of cinnamaldehyde with bupivacaine. For rats treated with 1% and 2% cinnamaldehyde plus 0.0625% bupivacaine, the time of complete recovery was 116.25±4.70 and 159.38±6.30 minutes. Accordingly, the nociceptive blockade is significantly prolonged as compared to 1% cinnamaldehyde (63.75±4.70 minutes), 2% cinnamal-

TABLE 1

Analgesic effects of cinnamaldehyde, lidocaine and bupivacaine.

| | Cinnamaldehyde | | | |
|---|---|---|---|---|
| | 0% (Vehicle) | 0.5% | 1% | 2% |
| Cinnamaldehyde alone | — | 43.13 ± 5.97 | 63.75 ± 4.70 | 95.63 ± 3.95 |
| Lidocaine 0.5% | 63.75 ± 3.75 | 65.63 ± 2.74[#] | 106.88 ± 3.40[#,*] | 157.50 ± 5.67[#,*] |
| Bupivacaine 0.0625% | 91.88 ± 4.43 | 78.75 ± 3.75[#,*] | 116.25 ± 4.70[#,*] | 159.38 ± 6.30[#,*] |

All data were presented as Mean ± SE.
[#]p < 0.05, compared with each selected concentrations of cinnamaldehyde.
[*]p < 0.05, compared with lidocaine or bupivacaine.

Example II

Co-administration of Cinnamaldehyde and Lidocaine

Lidocaine (0.5%) was given 10 minutes after the application of cinnamaldehyde to elucidate whether cinnamaldehyde prolongs the analgesic effect of lidocaine. Rat treated with 2% cinnamaldehyde and 0.5% lidocaine exhibited complete nociceptive block to pinpricks and the blockade lasted for about 15 minutes. Dose dependent analgesic effect was also observed in treatments in which the administration of cinnamaldehyde was followed by 0.5% lidocaine (FIG. 1; Table 1). Specifically, the time of complete recovery in rats treated with 0.5%, 1%, and 2% cinnamaldehyde plus 5% lidocaine was 65.63±2.74, 106.88±3.40 m and 157.50±5.67 minutes, respectively. By contrast, the time of complete recovery in rats treated with 0.5% lidocaine is about 63.75±3.75 minutes.

dehyde (95.63±3.95 minutes), or bupivacaine (91.88±4.43 minutes) alone (FIG. 2, Table 1).

Co-administration of 0.5% or 1% cinnamaldehyde plus 0.0625% bupivacaine did not produce obvious skin irritation. However, out of the eight rats treated with 2% cinnamaldehyde plus 0.0625% bupivacaine, two of them were discovered with mild irritation of skin redness approximately 24 hours later at the edge of the injection site.

Example IV

Lymphocytic Infiltration

Figure 3A:
FIGS. 3A-3E are photographs showing the skin cross-section obtained from rats treated in accordance with examples of the present disclosure.
Figure 3B:
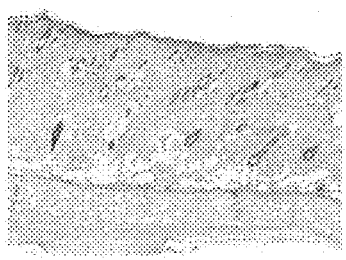
Figure 3C:
Figure 3D:
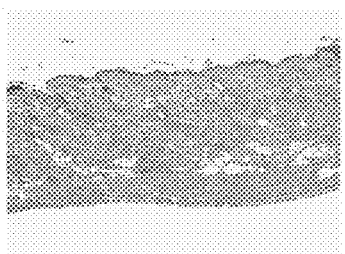
Figure 3E:
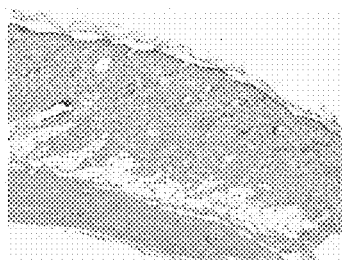

Tissue inflammation was evaluated by the level of lymphocytic infiltrations in the cinnamaldehyde-injected subcutaneous layer of rats' cross-sectioned skin at 48 h. More lymphocytic infiltrations appeared around two days after the injection of 1% (FIG. 3B) and 2% (FIG. 3C) cinnamaldehyde compared with 0.5% cinnamaldehyde (FIG. 3A), indicating inflammation at the injected area. However, this was not observed in the injected area for 40% DMSO (vehicle of cinnamaldehyde, FIG. 3D) and normal saline (vehicle of lidocaine/bupivacaine, FIG. 3E).

The foregoing results have demonstrated that cinnamaldehyde produced a dose-dependent cutaneous nocifensive blockade. Therefore, cinnamaldehyde is suitable for use as an analgesic drug. Furthermore, co-administration of cinnamaldehyde with at least one membrane permeable local anesthetic (such as lidocaine and bupivacaine) increased the potency and duration on subcutaneous analgesia, as compared with that produced by the local anesthetic or cinnamaldehyde alone. These results have revealed that cinnamaldehyde could be a potential anesthetic adjuvant to improve local anesthetic effects in both infiltration anesthesia/analgesia and topical application, such as EMLA® cream (2.5% lidocaine/2.5% prilocaine), LIDODERM® (lidocaine transdermal patch) and ELADUR® (bupivacaine transdermal patch).

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for prolonging analgesic effect of a membrane permeable local anesthetic in a human subject in need thereof, comprising administering to the subject an anesthetically effective amount of the membrane permeable local anesthetic and an effective amount of cinnamaldehyde for prolonging the analgesic effect of the membrane permeable local anesthetic in the subject, in the absence of a membrane impermeable compound that inhibits one or more voltage-gated ion channels when applied to the internal face of said channels but does not substantially inhibit said channels when applied to the external face of said channels, wherein the membrane permeable local anesthetic is an amide local anesthetic, and the cinnamaldehyde is administered at a dose of about 3-10 mg/kg body weight.

2. The method of claim 1, wherein the cinnamaldehyde is administered prior to or at the same time with the administration of the membrane permeable local anesthetic.

3. The method of claim 1, wherein the amide local anesthetic is lidocaine, mepivacaine, prilocalne, bupivacaine, levobupivacaine, ropivacaine, dibucaine, or articaine.

4. The method of claim 3, wherein the amide local anesthetic is lidocaine; and the lidocaine and the cinnamaldehyde are administered at a molar ratio of about 1:2 to 1:10.

5. The method of claim 3, wherein the amide local anesthetic is bupivacaine; and the bupivacaine and the cinnamaldehyde are administered at a molar ratio of about 1:20 to 1:85.

6. The method of claim 1, wherein the cinnamaldehyde is administered at a dose of about 4-10 mg/kg body weight.

7. The method of claim 1, wherein the membrane permeable local anesthetic and the cinnamaldehyde are administered subcutaneously, neuraxially, orally, topically, transdermally, or nasally.

* * * * *